(12) United States Patent
El-Hennawy et al.

(10) Patent No.: US 9,789,227 B1
(45) Date of Patent: Oct. 17, 2017

(54) LOCK SOLUTION FOR VENOUS CATHETERS USING SODIUM BICARBONATE

(71) Applicants: Adel Sayed El-Hennawy, Staten Island, NY (US); Elena Frolova, Woodmere, NY (US)

(72) Inventors: Adel Sayed El-Hennawy, Staten Island, NY (US); Elena Frolova, Woodmere, NY (US)

(*) Notice: Subject to any disclaimer, the term of this patent is extended or adjusted under 35 U.S.C. 154(b) by 95 days.

(21) Appl. No.: 14/641,078

(22) Filed: Mar. 6, 2015

(51) Int. Cl.
| | | |
|---|---|---|
| *A61K 31/727* | (2006.01) | |
| *A61L 29/02* | (2006.01) | |
| *A61L 29/16* | (2006.01) | |

(52) U.S. Cl.
CPC ............... *A61L 29/02* (2013.01); *A61L 29/16* (2013.01); *A61L 2300/102* (2013.01); *A61L 2300/404* (2013.01); *A61L 2300/42* (2013.01)

(58) Field of Classification Search
CPC .... A61L 29/02; A61L 29/16; A61L 2300/404; A61L 2300/42; A61L 2300/102
See application file for complete search history.

(56) References Cited

U.S. PATENT DOCUMENTS

| | | |
|---|---|---|
| 4,451,454 A * | 5/1984 | Wong ..................... A61K 33/00 424/422 |
| 4,500,309 A | 2/1985 | Diederich et al. |
| 5,032,615 A | 7/1991 | Ward et al. |
| 6,566,402 B2 | 5/2003 | Warnock |
| 7,132,413 B1 | 11/2006 | Pfirrmann |
| 8,703,739 B2 | 4/2014 | Kimura et al. |
| 8,747,911 B2 | 6/2014 | Gupta et al. |
| 2004/0185028 A1 | 9/2004 | Hu et al. |
| 2005/0255177 A1* | 11/2005 | Burgess ................. A61K 33/10 424/717 |
| 2014/0371171 A1* | 12/2014 | Souweine ....................... 514/56 |

* cited by examiner

*Primary Examiner* — Hasan Ahmed
(74) *Attorney, Agent, or Firm* — Michael I. Kroll; Edwin D. Schindler

(57) ABSTRACT

A Sodium Bicarbonate Catheter Lock Solution that prevents clot formation inside the catheter lumen and ensures patency of the catheter and also eliminates bleeding and other complications caused through the use of anticoagulants and other solutions as a catheter locking solution. Said lock solution may be used with or without other components such as antimicrobials/antibiotics and/or anti-coagulants/anti-clotting agents.

3 Claims, 5 Drawing Sheets

LOCK SOLUTION FOR VENOUS CATHETERS USING SODIUM BICARBONATE

BACKGROUND OF THE INVENTION

Field of the Invention

The present invention relates generally to use of intravascular catheters. More specifically, it relates to the use of central venous catheters. Even more specifically, it relates to hemodialysis catheters such as non-tunneled which are short term catheters and also tunneled which are long-term catheters.

More specifically, it relates to catheter lock solution which instills into the lumen of the catheter and helps to keep catheter patency between the times that it is not used for treatment of a patient.

Even more specifically, it relates to use of Sodium Bicarbonate solution as a catheter lock solution. The Sodium Bicarbonate Catheter Lock Solution prevents clot formation inside the catheter lumen and ensures patency of the catheter and also it eliminates bleeding and other complications caused through the use of anticoagulants and other solutions as a catheter locking solution.

Description of the Prior Art

There are various lock solutions for short term and long-term catheters to prevent both bacterial infection and clotting, which are the major problems with catheters and any evidence of catheter occlusion or thrombosis is dealt with immediately.

During the dwell time (the time between uses of the catheter) the hub and lumen of the catheter are filled with a locking solution. In many cases, anticoagulant or anti-clotting agent are added to locking solution to prevent clot buildup within the lumen of the catheter and to keep patency of the catheter. The most commonly used catheter lock solution is Heparin.

For example, heparin concentrates of between 1000-10000 U/ml may be added, however this may cause systemic anti-coagulation. To prevent this, other solutions have been used such as citrate, sodium chloride and many other solutions.

While these types of solutions may be suitable for the purposes for which they were designed, they would not be as suitable for the purposes of the present invention as heretofore described.

It is thus desirable to provide a catheter lock solution for catheters to mitigate the possibility of systemic anti-coagulation.

It is further desirable to provide a locking solution for catheters incorporating sodium bicarbonate to mitigate potential bleeding caused through use of anti-coagulants.

SUMMARY OF THE PRESENT INVENTION

Central venous catheters, originally introduced as vascular access for short-term dialysis, have been an acceptable form of permanent vascular access in some patients, particularly those with limited alternative options for vascular access. Approximately 17-18% of Hemodialysis patients select tunneled cuffed catheter as long-term vascular access.

The common method to ensure patency of the catheter is locking them with heparin at concentration of 1000 U/mL to 10,000 U/mL Each Hemodialysis center uses different concentration and there is no unified standard. However, when using a heparin lock solution for indwelling venous catheter, bleeding complications have been reported and heparin was found to alter coagulations studies.

The American Diagnostic and Interventional Society of Nephrology recommends locking catheter with a low concentration (1000 U/mL) Heparin solution or 4% trisodium citrate (TSC) as the method with relatively low bleeding risk.

Even after removing and discarding the catheter lock solution, the remaining heparin attached to the wall of lumens could have anticoagulation effect. Therefore, the overflowing heparin from catheters is an important reason of increased bleeding risk.

Preliminary testing shows Sodium Bicarbonate Catheter Lock Solution is very effective in preventing clotting of catheters, since it is not an anticoagulant and will not increase bleeding risk even when overflowing into circulation. Sodium bicarbonate solution, preferably 8.4% concentration, can be used as catheter lock solution for locking both non-tunneled, non-cuffed and cuffed, tunneled, hemodialysis catheters.

Effectiveness of Sodium Bicarbonate Catheter Lock Solution appears to be superior to Normal Saline Catheter Lock Solution in preventing catheter clotting in our clinical study.

Using Sodium Bicarbonate Catheter Lock Solution to flush and lock catheters is very safe and there were no observed side effects. Due to the risk of using heparin and citrate solution, Sodium Bicarbonate Catheter Lock Solution is clearly a safe way to lock catheters and would be a safer catheter lock method especially for patients with high bleeding risk.

Since there were no ideal catheter lock solutions, our study evaluated sodium bicarbonate as alternative catheter lock solution and found it to be inexpensive, available and easily popularized and mitigating the aforementioned bleeding issues caused by the anti-coagulant.

No studies were found using Sodium Bicarbonate Solution as a catheter lock solution, therefore, its anticoagulant principle cannot be definitively explained. It can be speculated that it works by binding calcium and removing it from the many enzymes of the coagulation system that require it as a co-factor.

Safety of using citrate solution as a catheter lock solution became an issue when the FDA reported death due to cardiac arrest shortly after ESRD patient received a rapid injection of 5 mL 47% citrate solution into one lumen of a central vein, tunneled catheter, just after placement, for the purpose of anticoagulation. However, the Medical Device Report (MDR), indicated that the patient did not expire immediately, but more than 24 hours later after receiving citrate catheter lock solution.

Study Conclusion: Sodium Bicarbonate solution may provide significant advantages for catheter lock in patients with all types of venous catheters, reducing catheter clotting and increasing retention rate without going into risks of using citrate or heparin.

A primary object of the present invention is to provide a catheter lock solution using sodium bicarbonate to overcome the aforementioned drawbacks in current catheter lock solutions.

Another object of the present invention is to provide a solution that can be used as a lock solution for any types of catheters.

Yet another object of the present invention is to provide a catheter lock solution for catheters both cuffed and non-cuffed including tunneled, non-tunneled and percutaneous catheters.

An additional object of the present invention is to provide a catheter lock solution using sodium bicarbonate that is easily available.

A further object of the present invention is to provide a catheter lock solution that will be inexpensive to administer.

Additional objects of the present invention will appear as the description proceeds.

The present invention overcomes the shortcomings of the prior art by providing an inexpensive and readily available anti-clotting component for venous catheter locking solution that largely eliminates catheter occlusion or thrombosis without leading to potential systemic bleeding that can be caused by regular use of anticoagulants.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

DESCRIPTION OF THE REFERENCED NUMERALS

Turning now descriptively to the drawings, in which similar reference characters denote similar elements throughout the several views, the figures illustrate the use of the present invention. With regard to the reference numerals used, the following numbering is used throughout the various drawing figures.

10 sodium bicarbonate solution
12 central catheter
14 catheter hub/port
16 heparin solution
18 citrate solution
20 sodium chloride solution
22 syringe-like applicator
24 catheter lumen

BRIEF DESCRIPTION OF THE DRAWING FIGURES

In order that the invention may be more fully understood, it will now be described, by way of example, with reference to the accompanying drawing in which.

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

Figure 1:
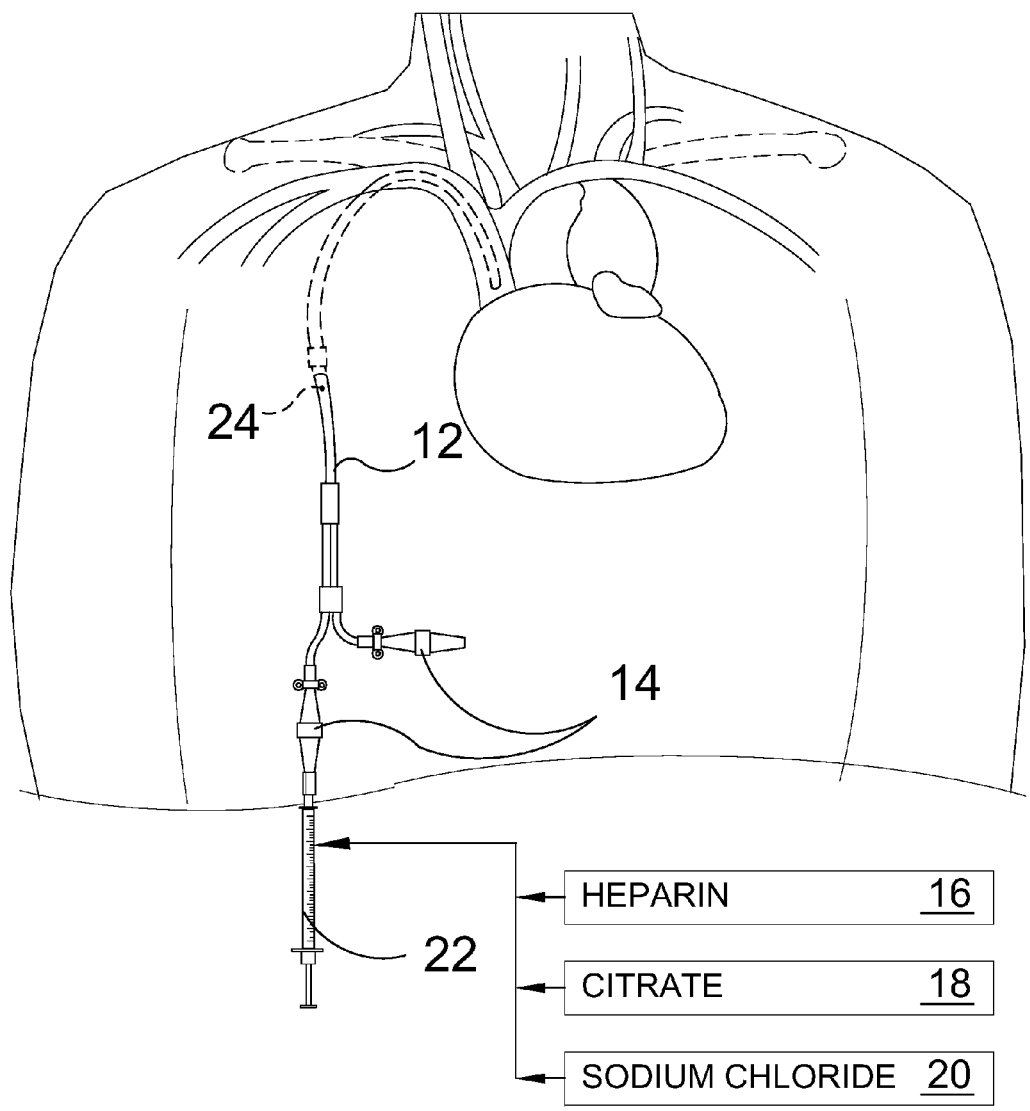
FIG. 1 is a illustrative view of the prior art.

Referring to FIG. 1, there is seen an illustrative view of the prior art. In the Figure there is shown a tunneled catheter as indicated at 12. Catheters whether short or long-term use maintained in the patient's body have a period of idle time, referred to as dwell or down time where one of the complications that can result is that the blood within the lumen 24 may clot. To combat this tendency, various solutions are currently inserted into the catheter and these solutions are called catheter lock solutions. They prevent clotting and, in many circumstances, are also intended to prevent infection by providing an antimicrobial solution or compound that rests within catheter lumen. These types of lock solutions would be injected or otherwise inserted into the catheter lumen by means 22, such as a syringe having a needle or fastener such as a leur lock.

In regard to prior art catheter lock solutions placed in the catheter lumen 24, compounds such as heparin 16, citrate 18, and sodium chloride 20, are used in various combinations and concentrations. As aforementioned, heparin has the disadvantage of possibly inducing bleeding (since it is an anticoagulant) and citrate solution also has potentially hazardous side effects.

Figure 2:
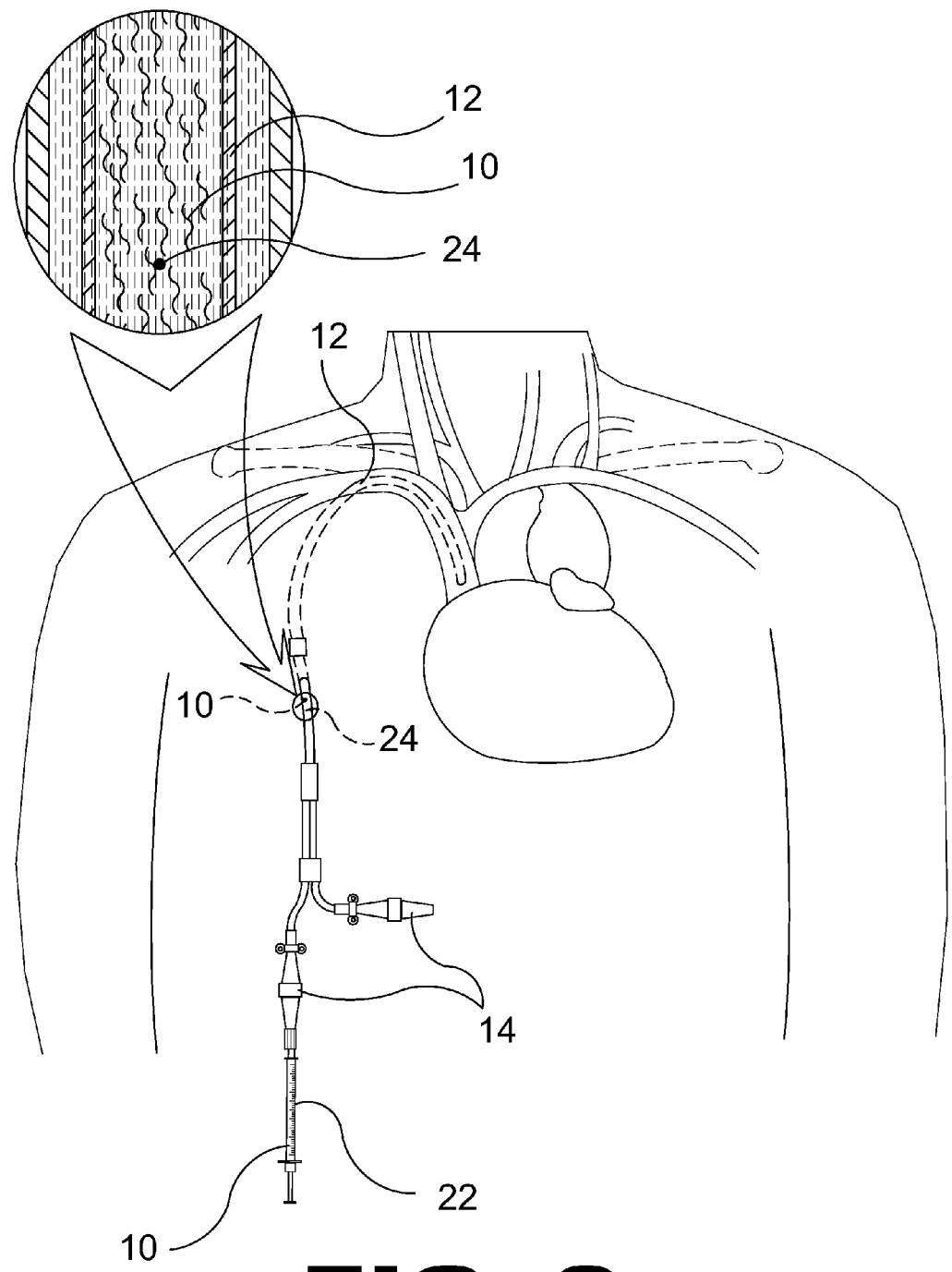
FIG. 2 is an illustrative view of the instant invention in use.

Referring now to FIG. 2 shown is an illustrative view of the present invention in use. The present invention provides a catheter lock solution to mitigate clotting of the catheter lumen 24 by inserting 22, 14 a Sodium Bicarbonate Catheter Lock Solution 10. It should be noted that the Sodium Bicarbonate Catheter Lock Solution will function by itself as a stand-alone anti-clotting lock solution or could be used in combination with an antimicrobial solution (not seen in the Figures) or even with an additional or supplementary anti-clotting or anticoagulant component.

Figure 3:
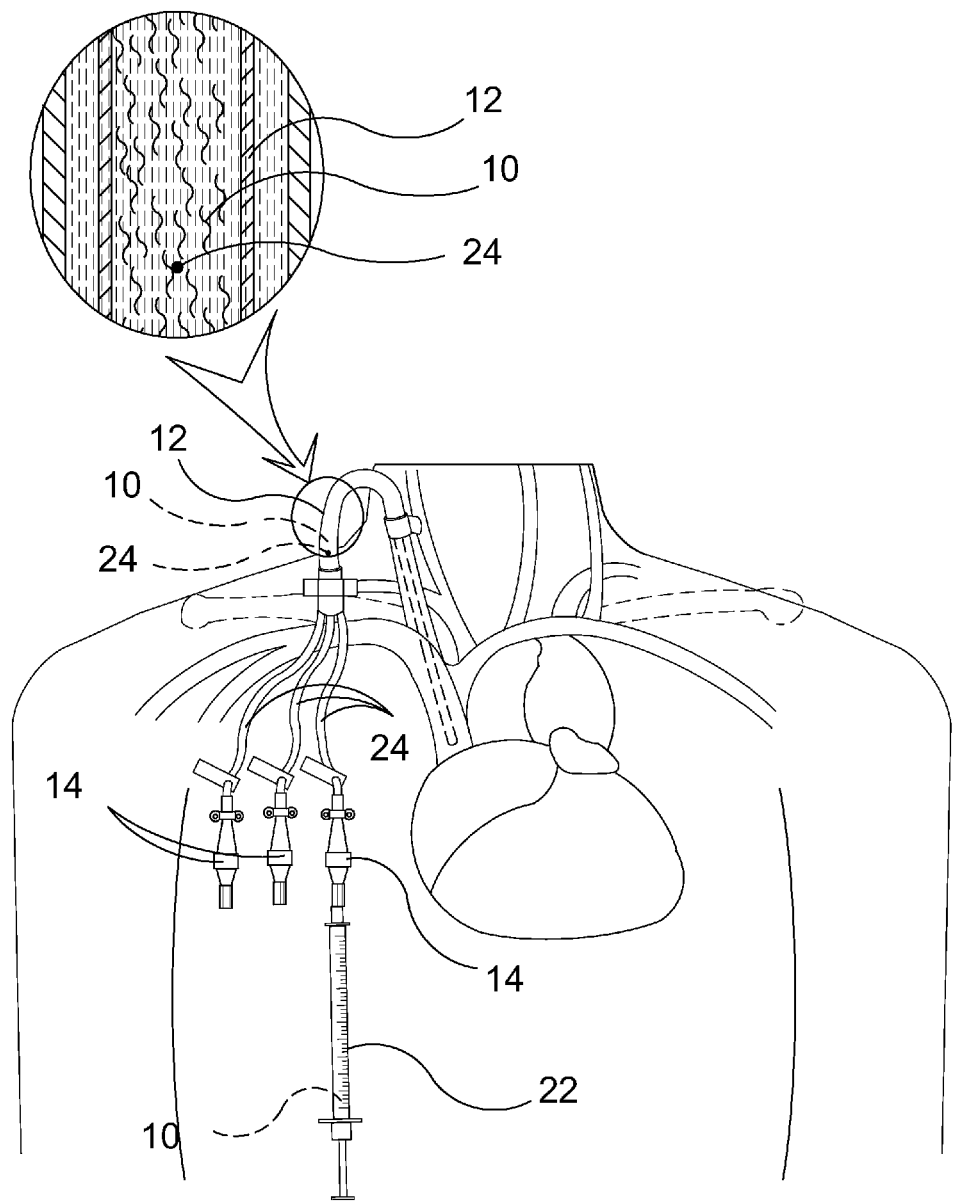
FIG. 3 is an illustrative view of a non-tunneled central catheter having a plurality of lumens.
Figure 4:
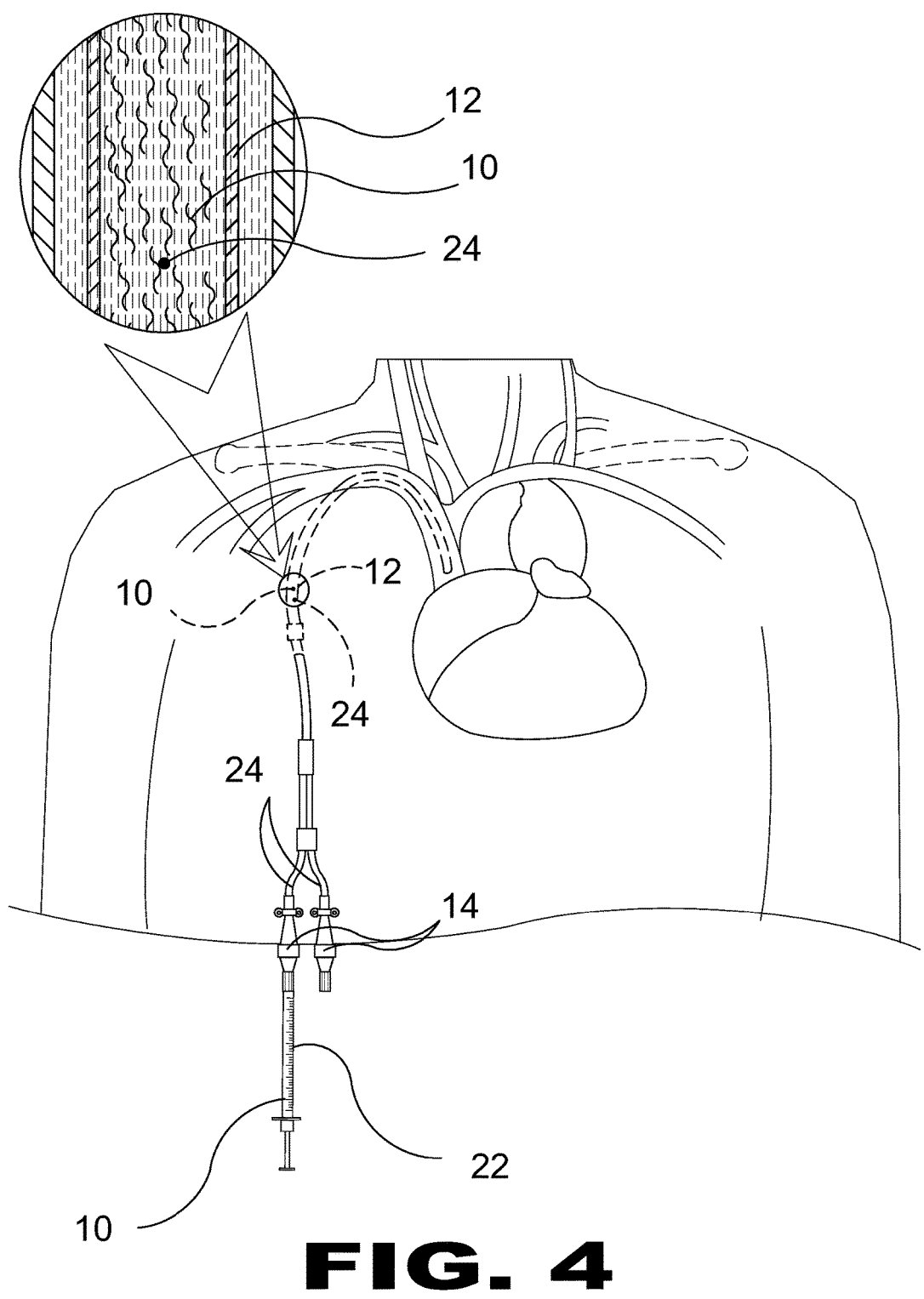
FIG. 4 is an illustrative view of a tunneled central catheter having a plurality of lumens.
Figure 5:
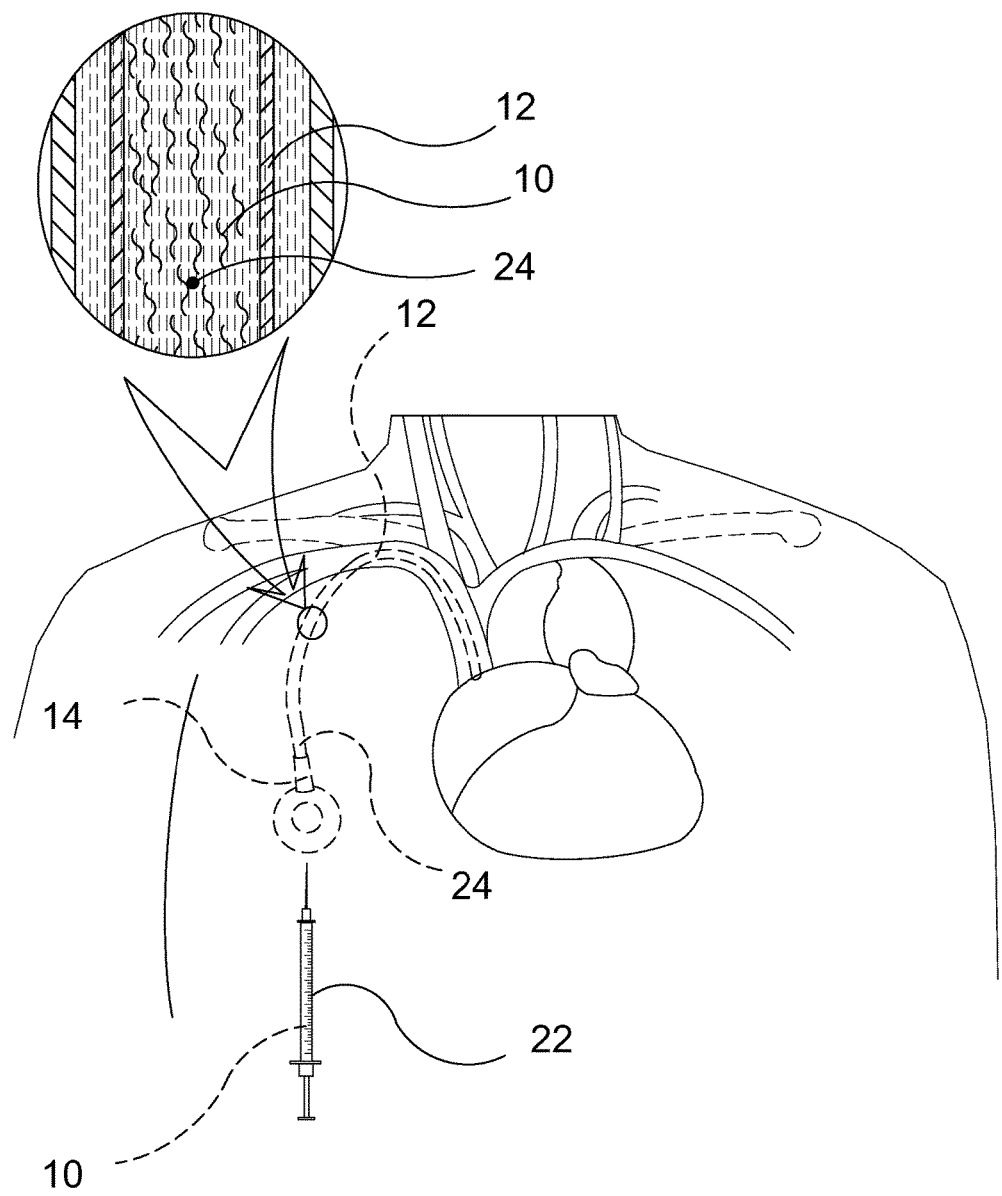
FIG. 5 is an illustrative view of a totally implanted central catheter having a subcutaneous port.

Referring to FIGS. 3 through 5, depicted are various types of vascular catheters having one or more lumen and use of the Sodium Bicarbonate Catheter Lock Solution therewith. A non-tunneled central catheter with single, double or triple lumen (FIG. 3) is shown placed percutaneously having the catheter exiting the skin in the vicinity of the venous cannulation with the different lumen infusing fluid through holes on the side of the catheter. A tunneled catheter, shown in FIG. 4.lies in a subcutaneous tunnel between the catherized vein and skin-exit site and may have a subcutaneous cuff approximate the exit site. A totally implanted venous access catheter having a subcutaneous port is shown in FIG. 5 with the catheter extending under the skin from the cannulated vein to an infusion port, which is accessed through needle puncture into the port's self-sealing septum. The Sodium Bicarbonate Lock Solution of the present invention can be use with any catheter requiring a lock solution to maintain patency.

No studies were found using Sodium Bicarbonate as a vascular lock solution, therefore, its anticoagulant principle cannot be definitively explained. It can be speculated that it works by binding calcium and removing it from the many enzymes of the coagulation system that require it as a co-factor.

It should be emphasized that Sodium Bicarbonate is readily available and inexpensive. Its availability is enhanced since it is commonly used for treatment of metabolic acidosis.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A method of preventing catheter occlusion or thrombosis in a catheter during dwell time, consisting of the steps of:

providing a patient with a central catheter for vascular access; and inserting into a lumen of said catheter a stand-alone anti-clotting lock solution consisting of 8.4% of sodium bicarbonate "and an antimicrobial agent" to mitigate clotting within said lock solution in order to keep patency when said catheter is not being used for treatment of a patient.

2. The method of preventing catheter occlusion or thrombosis in a catheter during dwell time of claim 1, wherein said catheter is a non-tunneled central catheter with single, double or triple lumen.

3. The method of preventing catheter occlusion or thrombosis in a catheter during dwell time of claim 1, wherein said catheter is a tunneled catheter adapted to lie in a subcutaneous tunnel.

* * * * *